United States Patent [19]
Adalsteinsson et al.

[11] Patent Number: 6,086,878
[45] Date of Patent: Jul. 11, 2000

[54] METHOD OF INCREASING MUSCLE PROTEIN AND REDUCING FAT IN ANIMALS

[75] Inventors: Orn Adalsteinsson, Kennett Square; Sandra G. Fitzpatrick-McElligott, Rose Valley; Jeffrey G. Hunchar, West Chester, all of Pa.

[73] Assignee: DCV, Inc., Wilmington, Del.

[21] Appl. No.: 08/915,627

[22] Filed: Aug. 21, 1997

[51] Int. Cl.$^7$ .......................... A61K 39/40; A61K 39/42; A61K 39/395; C12P 21/08

[52] U.S. Cl. ...................... 424/157.1; 424/158.1; 424/184.1; 424/185.1; 424/145.1; 424/130.1; 424/139.1; 424/809; 530/300; 530/311; 530/324; 530/325; 530/326; 530/327; 530/328; 530/387.9; 514/12; 514/16; 514/18

[58] Field of Search .......................... 424/157.1, 158.1, 424/184.1, 145.1, 130.1, 139.1, 185.1, 809; 530/300, 311, 387.9, 324–328; 514/12, 16, 18

[56] References Cited

U.S. PATENT DOCUMENTS

| | | |
|---|---|---|
| 4,599,229 | 7/1986 | Maccecchini . |
| 4,748,018 | 5/1988 | Stolle et al. . |
| 4,929,600 | 5/1990 | Cogburn . |
| 5,080,895 | 1/1992 | Tokoro . |
| 5,319,073 | 6/1994 | Wank . |
| 5,340,834 | 8/1994 | Stitt . |
| 5,367,054 | 11/1994 | Lee . |
| 5,739,106 | 4/1998 | Rink et al. . |
| 5,772,999 | 6/1998 | Greenblatt et al. . |
| 5,827,517 | 10/1998 | Cook et al. . |

FOREIGN PATENT DOCUMENTS

| | | |
|---|---|---|
| WO 98/03081 | 1/1998 | European Pat. Off. . |
| 9604011 | 2/1996 | WIPO . |
| 9604933 | 2/1996 | WIPO . |
| WO 96/40196 | 12/1996 | WIPO . |

OTHER PUBLICATIONS

D. J. Flint, "Immunological Manipulation of Adiposity", *Biochemical Society Transactions*, vol. 24, pp. 4–8.

Rudiger Schade et al., Polyclonal IgY Antibodies from Chicken Egg Yolk–an Alternative to the Production of Mammalian IgG Type Antibodies in Rabbits, 403–417.

Ed Harlow & David Lane, Choosing between Bacterial Expression and Peptides for Immunogen Production, *Antibodies A Laboratory Manual*, Chapter 5, 72–81, 1988 Cold Spring Harbor Laboratory.

A. Rodriguez–Sinovas, et al., Effect of cholecystokinin receptor antagonists on voluntary food intake in chickens, *Applied Animal Behaviour Science*, 40, 319–323, 1994.

C.T. Dourish, et al., Postponement of Satiety by Blockade of Brain Cholecystokinin (CCK–B) Receptors *Science Reports*, vol. 245, 1109–1111, Sep. 29, 1989.

Roger D. Reidelberger, et al., "Cholecystokinin supresses food intake by a nonendocrine mechanism in rats" *Cholecystokinin And Food Intake*, R901–R908, Apr. 6, 1994.

Carol L. McLaughlin, et al., "Effect of CCk Antibodies on Food Intake and Weight Gain in Zucker Rats" *Physiology & Behavior*, vol. 34, 277–282. 1985.

Clifton A. Baile, et al., "Hormones and feed intake" Proc. Nutr. Soc. (1983) vol. 42, 113–127.

John H. Walsh, "Gastrin" *Gut Peptides: Biochemistry and Physiology*, 1994, 75–76 and table of contents pp. v–vii.

Mary Anne Della–Fera, et al., "Cholecystokinin Antibody Injected in Cerebral Ventricles Stimulates Feeding in Sheep" *Science*, vol. 212, May 8, 1981.

*Primary Examiner*—Nita Minnifield
*Attorney, Agent, or Firm*—Basil S. Krikelis

[57] ABSTRACT

The invention is directed to a method and food product for achieving at least one of the following: increasing muscle protein or reducing fat in an animal. The method comprises administering to the animal an effective amount of a composition comprising a gastrointestinal neuro-modulator antibody in order to neutralize the gastrointestinal neuro-modulator.

12 Claims, No Drawings

METHOD OF INCREASING MUSCLE PROTEIN AND REDUCING FAT IN ANIMALS

BACKGROUND OF THE INVENTION

This invention generally relates to neutralizing or enhancing an endogenous hormone or peptide in a subject animal by administering an antibody or antibody-containing substance to the animal. More particularly, this invention relates to a method for reducing fat and improving the muscle yield in animals, specifically poultry, by administering, to said animals, antibodies to gastrointestinal neuro-modulators, such as cholecystokinin (CCK).

The production of food animals containing more muscle and less fat is a major goal of food providers. Animal food products are a major source of fat calories in the consumer diet, supplying about 36% of the calorie intake. Animal food products account for 57% of the fat consumed in the typical American diet and have been implicated as an important factor contributing to the development of heart disease and other related ailments. The American Cancer Society (1984), American Heart Association (1986) and the National Research Council (1982) have all recommended that only 30% or less of the total caloric intake of adults be in the form of fat. In particular, it has been concluded that the real solution to reducing fat intake lies in the production of leaner animals (*Designing Foods: Animal Product Options in the Marketplace,* Committee on Technological Options to Improve the Nutritional Attributes of Animal Products, Board on Agriculture, National Research Council, National Academy Press, Washington, D.C., 1988).

Successful attempts have been made at increasing muscle and reducing fat in animals. Some examples include anabolic steroids and growth hormones. However, both cause some related side effects, such as sterility, and in some cases, more serious side effects such as arthritis and gastric ulcers. In addition, there is a serious consumer concern over possible residual levels of anabolic steroids and growth hormones in the food product itself which has led to legislation in many countries proposing a ban on such treatments.

To avoid the problems associated with exogenous hormone administration, attempts have been made to regulate animal growth immunologically, by actively immunizing the animal against a specific component or hormone, the lack of which promotes the development of a relatively lean animal (Flint, D. J., et al. *Hannah Res.*, pp. 123–127 (1985)).

The gastrointestinal (GI) tract is equipped with a large endocrine gland, through which its endocrine cells synthesize and secrete a variety of biologically active peptide hormones which we have designated as gastrointestinal (GI) neuro-modulators. A significant body of evidence suggests that GI neuro-modulators are released from the stomach, duodenum and small intestine into the lumen of the GI tract. Some GI neuro-modulatory peptides include cholecystokinin (CCK), bombesin, gastrin, neuropeptide Y, urocortin, corticotropin-releasing factor, and somatostatin, among many others.

The cholecystokinin (CCK) family of peptides has been shown in the prior art to negatively affect food intake and thus inhibit growth in both mammals (Gibbs et al, 1973) and birds (Savory and Hodgkiss, 1984). The sulfated tyrosine residue, which is contained within CCK-8, has been shown to be important for biological activity. Antibodies to naturally occurring CCK peptide have been successfully produced endogenously in pigs (Pekas and Trout, 1990; Pekas 1991) and rats (MacLaughlin et al, 1985). In both species, the adverse effects of CCK on food intake and weight gain were prevented by endogenous circulation of CCK antibodies.

Antibodies can be orally, intravenously or otherwise administered to a subject animal. This process is generally referred to in the art as passive transfer. The antibodies to be transferred generally are derived from milk, colustrum, serum, egg yolk and even monoclonal antibodies from hybridomas. An example of passive transfer occurs when maternal antibodies are passively transferred to newborn mammals through the placenta and during nursing through colustrum and milk. By this method, the young animals obtain protection and natural immunity against harmful antigens in the environment. Similarly, for developing avians, reptiles and other egg laying animals, egg yolk is the source of maternal antibodies.

Recently, therapeutic studies have successfully exploited oral administration of antibodies for the treatment of some infectious diseases. By a process of vaccination, animals can be immunized against specific microorganisms and other antigens. In addition, increased titers of antibodies can be obtained by a process of hyperimmunization. High amounts of specific antibodies can be obtained by immunizing animals with specific antigens and isolating the antibodies from the egg yolk, milk, colustrum or serum.

There are five distinct classes of antibodies which are also called immunoglobulins (Ig). The most abundant is IgG. The other four are IgM, IgA, IgD, and IgE. These antibodies combine with the antigen and act to neutralize or counter the effects of the antigen introduced into the animal. They accomplish this result by binding to the antigen thereby neutralizing it and preventing it from binding to other specific cell receptors. The main immunoglobulin present in egg yolk is called IgY, which is similar to IgG but possesses considerable temperature and acid resistance.

Egg, and milk preparations serve as practical source of antibodies suitable for consumption by animals. In fact, egg yolks, for example, can contain as much as 100 mg of antibody, and large numbers of antibody-laden eggs can be produced in a relatively short period of time. Since vaccination of an animal can be used to develop such increased antibody titers in milk and eggs, such immunized milk and eggs can be fed to subject animals whereby antibodies are passively transferred to the subject animals to confer immunity and protection against microorganisms. Antibodies can be used not only to fight off pathogenic antigens or other foreign molecules but can be used, as described herein, to neutralize naturally occurring proteins and thereby modulate that protein's normal physiological effect on the animal's system.

Accordingly, antibodies can be used to bind to molecules such as CCK and somatostatin, as well as receptors, hormones and other gastrointestinal neuro-modulators in the gastrointestinal tract, nervous system and other body systems in general, to alter their effect.

There is a need for method of increasing muscle and/or reducing fat in an animal using a safe nutritional food source. The present invention provides a method for modulating the gastrointestinal function, using antibodies to improve meat yield and/or reduce fat in animals.

SUMMARY OF THE INVENTION

The invention relates to a method for achieving at least one of the following: increasing muscle protein or reducing fat in an animal, the method comprising administering to the animal an effective amount of an antibody.

In another embodiment, the invention relates to a method for achieving at least one of the following: increasing muscle protein or reducing fat in an animal, which comprises administering to the animal an effective amount of a composition comprising a gastrointestinal neuro-modulator antibody.

In yet another embodiment, the invention relates to a method of achieving at least one of the following: increasing muscle protein or reducing fat in an animal, the method comprising neutralizing or enhancing an endogenous gastrointestinal neuro-modulator in said animal.

In still another embodiment, the invention relates to a food product for achieving at least one of the following: increasing muscle protein or reducing fat in an animal, the food product comprising an effective amount of a composition comprising an antibody.

In a more particular embodiment, the invention relates to a food product for achieving at least one of the following: increasing muscle protein or reducing fat in an animal, the food product comprising an effective concentration of a gastrointestinal neuro-modulator receptor antibody.

In an additional embodiment, the invention relates to a method for achieving at least one of the following: increasing muscle protein or reducing fat in an animal, the method comprising administering to said animal a composition obtained from an animal immunized with a gastrointestinal neuro-modulator.

DETAILED DESCRIPTION OF THE INVENTION

Definitions

The term "gastrointestinal (GI) neuro-modulator" means any composition which influences gastrointestinal motility, including regulatory peptides, neurotransmitters, hormones and immune-regulators, among others. Some examples include cholecystokinin (CCK), bombesin, somatostatin and gastrin among many others.

The term "gastrointestinal (GI) neuro-modulator receptor" means a receptor which binds with a gastrointestinal neuro-modulator as defined above.

The term "cholecystokinin or CCK" refers to the biologically active peptide and any other form of the peptide including, but not limited to, peptides of different lengths, esterified, hydroxylated, sulfated, fluorinated or non-amide derivatives that bind the CCK receptor.

The term "CCK-8"refers to the biologically active octapeptide which forms the amide portion of the longer peptide and generally consists of the following amino acids:

Asp-try($SO_3$)-Met-Gly-Trp-Met-Asp-Phe-$NH_2$ (SEQ ID NO:1).

The CCK-8 peptide can also be in a non-amide form.

The term "gastrointestinal neuro-modulator antibody" refers to an antibody which binds to a gastrointestinal neuro-modulator.

The term "gastrointestinal neuro-modulator receptor antibody" refers to an antibody which binds to a gastrointestinal neuro-modulator receptor.

The term "egg or fraction thereof" means any whole egg (table, hyperimmunized or otherwise) or any product derived therefrom.

The term "table egg or fraction thereof" means a whole egg, or any product derived therefrom, obtained from egg-producing animals which are not maintained in a hyperimmune state.

The term "hyperimmunized egg or fraction thereof" means whole egg or any product derived therefrom, obtained from an egg producing animal maintained in a hyperimmune state.

The term "milk or faction thereof" means milk, or products derived therefrom, obtained from a milk-producing animal which is not maintained in a hyperimmune state.

The term "hyperimmunized milk or fraction thereof" means milk, or products derived therefrom, obtained from a milk-producing animal which is maintained in a hyperimmune state.

The term "encapsulating composition" means a composition capable of and used for completely surrounding another composition or compound as if in an envelope or a capsule, thus not allowing any foreign material to reach the other composition or compound until the encapsulating composition has dissipated.

The term "gastrointestinal (GI) neuro-modulator neutralization" means any method which uses compositions containing antibodies that bind to or interact with gastrointestinal neuro-modulators or their receptors to change or modify their action.

The term "animal" means all vertebrates including fish, avians, amphibians, reptiles and mammals (including humans).

The term "subject animal" refers to the animal which is to be administered the antibody produced by the target animal. For example, in the case of peptide neutralization, the subject animal will be administered antibody until the effect is observed.

The term "target animal" refers to an animal which is to be used as the antibody producing animal. For example, if one desires production of antibody within an egg, then an avian will be the target animal.

The term "weight gain" means an increase in weight.

The term "weight loss" means a decrease in weight.

The term "feed efficiency" expresses the efficiency by which an animal converts feed into weight gain. Feed efficiency is expressed as the ratio of weight of feed to weight gain.

The term "increased muscle protein or increased muscle yield" means an increase in the amount of salable meat (i.e. muscle not fat) available in an animal. In particular, increased muscle protein or yield is generally expressed as the percentage increase in salable meat per pound of animal.

The term "fat reduction" means a reduction in the total amount of fat in an animal. Fat reduction generally may go hand-in-hand with increased muscle yield. As muscle yield increases, fat content is generally reduced in animals of similar weight.

The Invention

The invention relates to neutralization or enhancement of at least one type of endogenous gastrointestinal (GI) neuro-modulator in an animal by administration of antibodies against said GI neuro-modulator or its receptor which increases muscle yield and/or reduces fat in said animal. Although the invention is particularly suited for food animals such as poultry, bovine, ovine, and swine, the invention is applicable to all animals and humans, and particularly those suffering from malnutrition caused by diseases (such as diarrhea, HIV), gastrointestinal disorders, eating disorders and famine.

In a preferred embodiment, the invention comprises a method of reducing fat and improving meat or muscle yield in an animal which comprises administering to the animal an effective concentration of a specific GI neuro-modulator, and preferably, cholecystokinin (CCK) antibody. In particular, the CCK antibody is produced naturally by immunizing an avian or bovine. The recovered antibodies are transferred naturally to the egg or milk of the avian or bovine, and this antibody containing egg or milk is subsequently administered to the subject animal.

By administering CCK antibody produced in such a manner, applicants are providing a natural food product for increasing muscle protein and reducing fat in a subject animal without the fear of side effects (excluding, of course, general allergies to eggs or milk). The amount of antibody-containing egg, egg yolk or milk to be added to the feed will vary with the species, size and age of the animal. However, since egg and milk are natural foods and non-toxic, the amount which can be administered is not critical, so long as it is enough to be effective.

Preparation and administration to animals of antibodies to any GI neuro-modulators, for reducing fat and increasing muscle protein, is encompassed by the method of this invention. In particular, it is believed that antibodies produced to any gastrointestinal neuro-modulator, its receptor, or their subunits, increase muscle yield by blocking the interaction of the gastrointestinal neuro-modulator with its receptors in the gastrointestinal system and available receptors in the CNS.

Gastrointestinal Neuro-Modulators

As referred to briefly in the background of the invention, there are many gastrointestinal (GI) neuro-modulators which have similar physiological effects in mammalian and avian systems. Some of these GI neuro-modulators which can be used in the method and food product of the invention include acetylcholine, cholecystokinin (CCK), bombesin, somatostatin, neuropeptide-Y, urocortin, corticotropin-releasing factor, substance P, 5-hydroxytryptamine, vasoactive intestinal polypeptide, enkephalins, neurotensin, secretin, motilin, gastric inhibitory peptide, gastrin releasing peptide and gastrin, among many others.

The preferred neuro-modulator used in the invention is the CCK peptide. In actuality, endogenous CCK consists of a family of peptides, where the predominant molecular form exists in sulfated and desulfated forms and is an octapeptide (CCK-8) hormone. CCK, which is normally released from the nerves of the enteric nervous system, after a meal is consumed, increases transit time in the gastrointestinal tract. CCK peptide has several receptors which can be subdivided into at least two subtypes, $CCK_A$ and $CCK_B$ on the basis of pharmacological studies. A $CCK_A$ receptor subtype predominates in the gastrointestinal system but occurs also in highly localized areas of the rat CNS, where it modulates feeding and dopamine-induced behavior. $CCK_B$-type receptors have also been described outside the CNS in gastrointestinal smooth muscle cells, where they modulate gallbladder and bowel motility. Both CCK family of peptides and their receptors are widely distributed throughout the gastrointestinal and central nervous systems where they regulate secretion, motility, growth, anxiety, and satiety.

By its action, the CCK peptide controls the rate at which the food travels through the intestine by causing an increase in intestinal contractions. The presence of CCK also alters the willingness to eat. CCK is responsible for what is known as the satiety effect which is a physiological effect that sharply decreases an animal's appetite. If an antibody combines with CCK, CCK is neutralized, the satiety effect is inhibited and adverse effects of endogenous CCK on gastrointestinal motility are averted. In addition, if antibodies bind to the receptor for CCK, and in particular the $CCK_A$ receptor, they will also neutralize the affect of CCK. In other words, CCK-receptor binding antibodies will reduce intestinal mobility and inhibit the satiety effect. Basically, the animal will eat more and increase absorption of nutrients.

The endocrine and immune systems can also influence gastrointestinal motility by actions of cytokines and hormones. The gastrointestinal mucosa is itself an endocrine organ and is responsible for the release of such hormones as gastrin, secretin, cholecystokinin, motilin, gastric inhibitory peptide, neurotensin, and gastrin-releasing peptide, among others. During feeding, irregular phasic contractions serve to mix intestinal contents and move them slowly in a direction away from the mouth. The rate at which phasic contractions occur is determined by the excitability of the smooth muscle cells and by local slow waves which are influenced by these compounds.

Neuropeptide Y, Bombesin, somatostatin and gastrin have similar physiological effects on the gastrointestinal tract as CCK. These gut hormones have effects on nutrient uptake, gastrointestinal mobility and they alter feeding behavior. In addition, these gut hormones also act as neurotransmitters in the brain and modify physiological functions, both peripherally and centrally. It is of note that several of these peptides exist in different molecular forms and in some cases, such as CCK and gastrin, may resemble each other in molecular structure.

It has been determined that antibodies to any of the above-mentioned neuro-modulators and/or their receptors are effective for use in increasing muscle protein and reducing fat in an animal as described by this invention. In addition, antibodies to peptides of various lengths or adequate substitutions, such as, for example, the sulfated tyrosine of CCK-8, are also contemplated as effective for use in this invention.

Preparation of a Vaccine

Antibodies can be produced in a variety of ways known to those having skill in the art. Some preferred methods include vaccination, inoculation or immunization of an animal to elicit an immune response. An immune response is elicited in an animal by, for example, administration of an antigen or antigens (i.e. a vaccine) to said animal. The animal will naturally respond by producing antibodies to those antigens, i.e. an immune response.

In some cases, an antigen may not be of a sufficient size to effectively or optimally elicit an immune response. In fact, it is generally preferred in the art that a composition having a molecular weight of 10,000 Daltons be used to elicit an immune response. As such, certain modifications must be made to the antigen. For example, isolated CCK peptide has a molecular weight less than 1,500 Daltons. In order to achieve optimal immunogenicity, it is preferred that the CCK peptide be coupled chemically or through recombinant molecular techniques to larger "carrier" molecules. Examples of "carrier" molecules which make a peptide more immunogenic include ovalbumin, bovine gamma globulin (BGG), keyhole limpet hemacyanin (KLH), mouse serum albumin and rabbit serum albumin, among others. Due to its small size, it is preferred that the CCK peptide be conjugated with a carrier protein having a molecular weight of approximately 8,000 Daltons or more in order to form a conjugate of a size capable of eliciting an immune response.

A preferred method of coupling the CCK peptide to a larger protein carrier to form an immunogen is as follows. The CCK peptide is covalently coupled to a purified carrier protein, such as bovin immunoglobulin G (IgG). Electron-microscopy grade gluteraldehyde [$O=CH-(CH_2)_3-CH=O$] is preferably used as a homofunctional coupling reagent, where the aldehyde groups form an irreversible bridge between the N-terminal amino group of the peptide and the available amine groups of the protein carrier molecule. This procedure can be applied as a single step wherein the peptide is simultaneously reacted with gluteraldehyde and bovine IgG in the presence of 10 mM sodium acetate, pH 7. Glycine is then added in order to quench any unreacted aldehyde groups that may still be present. The peptide is then dialyzed and a protein assay is performed to determine the concentration of the peptide. The preparation is then preferably aliquoted and stored frozen.

Once a suitable form of the antigen is available for immunization, it can then be used to formulate a vaccine. For example, in the case of CCK peptide, the conjugated peptide can be formulated as an adjuvant-based vaccine. This vaccine can then be used to elicit antibody production in a target animal. A typical adjuvant which can be used is Freund's complete adjuvant. If mammals comprise the target animal, then subsequent inoculations should consist of incomplete adjuvant. Other suitable adjuvants include those as referenced in *A compendium of vaccine adjuvants and excipients,* Vogel, F. R. and Powell, M. F. (1995); *In Vaccine Design, The Subunit and Adjuvant Approach,* Powell, M. F. and Newman M. J. eds Plenum Press N.Y., as well as others as are known by those having ordinary skill in the art. Amounts and concentration of adjuvant are readily determined by those having ordinary skill in the art.

Production of Antibody

It is preferred that, for purposes of gastrointestinal neuro-modulator neutralization, the target animal either be an egg-producing animal or a milk-producing animal and more preferably, an avian, ovine or a bovine. Avians, ovines and bovines are preferred because they produce an easily administered form of the antibody (i.e. the milk or egg itself). As is well known to those having skill in the art, once an immune response is elicited, antibodies are produced and are transferred to the eggs or milk of the immunized avian or mammal.

Chickens are the most preferable source of the eggs, although any egg-producing animal can be used. Other suitable egg-producing animals include turkeys, geese, ducks, reptiles, amphibians and the like. As for milk-producing animals, dairy cows are preferred, although other milk-producing animals contemplated by this invention include goats, sheep, buffalo or llamas, among others. In addition to eggs and milk, antibodies can be obtained from whole blood, plasma or serum from any inoculated animal.

In a preferred embodiment, the production of CCK antibody is accomplished by utilizing known immunization technology for producing antibodies in egg yolks of avians or other egg-producing animals. Specifically, hens are challenged by injection with CCK peptide which is conjugated to a carrier protein as described above. In response to exposure to the conjugated CCK peptide, the eggs laid by these hens will contain high levels of CCK antibody in the yolk.

Larger quantities or supranormal levels of an antibody can be generated by hyperimmunizing the target animal. In particular, if, for example a chicken is chosen as the target animal, the chicken would be brought to a specific state of immunization by means of, for example, periodic booster administrations of sufficiently high dosages of a gastrointestinal neuro-modulator. The preferred dosage range should be equal to or greater than the dosage necessary to cause a primary immune response. Hyperimmunization procedures are well-known in the art and have been described in detail (see U.S. Pat. No. 4,748,018).

Alternate modes of hyperimmunizing target animals can be used in place of gastrointestinal neuro-modulator vaccines, and include the use of genetic vaccines. In particular, any DNA construct (generally consisting of a promoter region and an antigen encoding sequence) will trigger antibody release. Genetic vaccines consist of antigen-coding vectors, fragments of naked DNA, plasmid DNA, DNA-RNA antigens, DNA-protein conjugates, DNA-liposome conjugates, DNA expression libraries, and viral and bacterial DNA delivered to produce an immune response. Methods of DNA delivery include particle bombardment, direct injection, viral vectors, liposomes and jet injection, among others. When applying these delivery methods, much smaller quantities are necessary and generally result in more persistent antigen production. When using such genetic processes, the preferred method for introducing DNA into avians is through intramuscular injection of the DNA into the breast muscle.

Any form of the neuro-modulator can be administered to the target animal to illicit an immune response, including purified and synthesized neuro-modulator. Well known means in the art can be used for purifying the neuro-modulator such as known peptide synthesis techniques including fractionation, chromatography, precipitation or extraction. Peptide synthesis is well known in the art, and adequate synthesis systems are available from several commercial sources (i.e. PerSeptive Biosystems, Inc., Framingham, Mass. 01701).

For administration to the target animal to elicit an immune response, a particular embodiment is contemplated in which the CCK peptide is encapsulated prior to administration. Generally, it is preferred that the CCK peptide-containing, shaped encapsulating matrix materials are formed from polymers of biocompatible material, or, more preferably, biodegradable materials such as polylactic acid, polyglycolic acid, copolymers of lactic acid and glycolic acids, polycaptolactone, copolyoxalates, proteins such as collagen, fatty acid esters of glycerol, and cellulose esters. These polymers are well known in the art and are described, for example, in U.S. Pat. Nos. 3,773,919, 3,887,699, 4,118,470, and 4,076,798.

In one embodiment, hyperimmunization of an animal is achieved by a single administration of a microencapsulated vaccine. The feeding of a microencapsulated vaccine results in a constant, pulsed release of the vaccine into the animal and eliminates the need for repetitive injections. In addition, a greater immune response, as measured by antibody production, is achieved using a controlled release vaccine. Many different composition for the slow release of vaccines have been described which would be applicable to the method of the invention, for example, as described in Sanders, H. J., *Chem. & Engineering News,* Apr. 1, 1985, pp. 30–48.

Other sources of antibody production include cell fusion using hybridoma techniques, genetically altered cell cultures and fermentation using recombinant technology, among others.

Administration of the Antibody

Once the antibodies are produced, they can then be administered to a subject animal to neutralize the particular gastrointestinal peptide or its receptor and thus increase muscle protein and reduce fat. While eggs, and more preferably, hyperimmunized eggs, are the preferred source of massive quantities of antibodies, it is possible, as stated earlier, to collect the antibodies from milk, whole blood, plasma or serum of the target animal.

Antibodies can be isolated and purified from the egg or milk producing animals or their respective eggs or milk, by the methods known in the art. A number of methods for the extraction of antibodies from egg yolk have been described. Polson et al 1985 and Jensenius et al. 1981 successfully used polyethylene glycol and sodium dextran sulfate respectively as protein precipitants in the isolation of pure immunoglobulin from egg yolks. Yokoyama et al. 1992 obtained the water soluble protein fraction after the lipid components were precipitated with an aqueous dispersion of acrylic resins. Lee (U.S. Pat. No. 5,367,054, 1994) describes a high purity and high yield method for isolating and purifying immunoglobulins or fragments thereof from egg yolk by extracting the yolk with a composition containing one or more medium-chain fatty acids.

The GI neuro-modulator antibody of the present invention is administered to a subject animal by any means that increases muscle protein and/or reduces fat in the subject animal. It is preferred that administration occur by feeding egg or egg yolk from vaccinated egg-producing animals or milk from vaccinated milk-producing animals. Egg, egg yolk and milk are natural food ingredients and are non-toxic and safe.

Other embodiments include administering purified antibody parenterally, subcutaneously, intravenously, intramuscularly, intraperitoneally, intranasally, or orally.

In the case where the GI neuro-modulator antibody is produced in the egg of an immunized avian, it is preferred that the egg itself, which contains the GI neuro-modulator antibody, either functions as, or be processed into, a food product. One preferred method for preparing the egg to be processed into a food product involves drying the egg into an egg powder. Although various methods are known for drying eggs, spray drying is a preferred method. A temperature of no more than 140 F. (60 C.) is preferably used. Samples are monitored for moisture content during the drying process to obtain a final product having any consistency desired.

The dried egg powder can be mixed with food animal feed rations or sprayed directly onto food pellets preferably in oil and thus fed directly to food animals in a simple fashion. Referring to the CCK antibody, typically, 0.1 to 1 CCK antibody-containing egg of this invention is used per 8 pounds of feed. In the case of poultry, spray-dried egg yolk powder is typically sprayed or mixed into poultry feed at 50–500 grams per ton, consistent with maintaining antibody titers sufficient to increase muscle protein and reduce fat in the subject animal.

The dried egg powder can also be used in drinks, protein supplements and any other nutritional, athlete-associated products which are particularly suited to human consumption. In addition, the egg powder can be used in bake mixes, powder bars, candies, cookies, etc.

For increased or improved effect, a synergistic effect can be achieved by administering the GI neuro-modulator antibody in combination or coincidingly with other antibiotics and growth promoting substances. Antibiotics and growth promoting substances, such as flavomycin, are well known in the art, and those having skill in the art can readily determine appropriate dosages to administer to the subject animals.

Alternatively, whole eggs may be administered to the subject animal or if desired the whole egg can be eaten raw. In other words, there is no need to separate the yolk from the albumin, except to achieve higher concentrations of the antibody.

In the case of administering purified antibody, oral administration is the preferred method and is preferably accomplished through solid dosage forms which include capsules, tablets, pills, powders and granules, among others. In solid dosage forms, the GI neuro-modulator antibody is preferably admixed with at least one inert diluent such as sucrose, lactose, starch or fat. Such dosage forms can also comprise, as is normal practice, additional substances other than the diluent. In the case of capsules, tablets, and pills, the dosage forms may also comprise buffering agents, pH sensitive polymers, or any other slow-releasing encapsulating compositions which are typically used for encapsulation purposes in the food and drug industry. Tablets and pills can alternatively be prepared with an enteric coating.

Liquid dosage forms of the GI neuro-modulator antibody for oral administration preferably include pharmaceutically acceptable emulsions, solutions, suspensions, syrups and elixirs, containing inert diluents commonly used in the pharmaceutical art. Besides inert diluents, compositions can also include wetting, emulsifying, suspending, and sweetening agents.

Preparations of the GI neuro-modulator antibody for parenteral administration preferably include sterile aqueous or non-aqueous solutions, suspensions or emulsions. Examples of nonaqueous solvents or vehicles are propylene glycol, polyethylene glycol, vegetable oils such as olive oil and injectable organic esters such as ethyl oleate.

The dosage of active ingredients may be varied; however it is necessary that the amount of the active ingredient shall be such that an effective dosage form is delivered. It will be recognized that the selected dosage form depends upon the desired therapeutic effect, the route of the administration and the duration of the treatment.

Administration dosage and frequency will depend on the size, age and general health condition of the subject, taking into consideration the possibility of side effects. Administration will also be dependent on concurrent treatment with other drugs and subjects' tolerance of the administered drug.

Effective Amounts

The exact amount of antibody and antibody containing composition to be administered of course depends on the animal, the amount of specific antibody present, the route of administration and the age and size of the animal. In the preferred embodiment, administration to a subject of a CCK hyperimmunized egg or fraction thereof, it has been determined, and is detailed in the examples to follow, that the preferred dose range of hyperimmunized egg or fraction thereof to be given to a subject animal is between 0.1 and 3 eggs per day. In addition, typically, 0.1 to 1 CCK containing eggs are used per 8 pounds of feed for effectively increasing muscle protein and reducing fat in poultry. Dried egg yolk powder is typically added to human food or animal feed at 0.007% to 10 % dry weight. The upper limit of egg which can be administered is not critical because immunized eggs are relatively non-toxic and are normal constituents of the human and animal diet.

When feeding spray-dried egg yolk powder specifically to poultry, the powder is typically sprayed or mixed into feed at 50 –500 grams per ton.

Effective antibody amounts to be administered to a subject animal generally range from 1 $\mu$g to 50 mg of antibody per kg of the subject animal's body weight.

Applications of the Antibody

The antibodies and antibody-containing compositions of this invention is used to increase muscle protein and reduce fat in any animal, and more preferably, in an animal which functions as a source of food. Some sources which benefit include poultry, including chickens and turkeys; mutton and lamb from sheep; beef and veal from cattle; pork from pigs; and rabbit. With regard to all animal groups, and, in particular, humans, the antibodies and antibody-containing compositions of the invention increase muscle yield and reduce fat in animal groups suffering from gastrointestinal disorders, eating disorders, hormonal disorders, famine, and malnutrition caused by diseases such a diarrhea and HIV, among others;

The antibodies and antibody-containing compositions of the invention are further applicable to control weight in domestic animals and pets, such as cats, dogs, horses, rabbits and the like.

Additionally, the antibodies and antibody-containing compositions of the invention are effective in improving athletic performance in humans and thoroughbreds, among others.

Having now generally described this invention, the same will be further described by reference to certain specific examples which are provided herein for purposes of illustration only and are not intended to be limiting unless otherwise specified.

EXAMPLES

Example 1

Eliciting CCK-8 Antibodies in Eggs

Methods

CCK-peptide vaccines were prepared by conjugation of synthetic cholecystokinin (CCK-8) (SEQ ID NO:1) (Fragment 26-33 amide with sulfated tyrosine) to bovine gamma globulin (BGG) using glutaraldehyde. The vaccines were emulsified with Freund's complete adjuvant (1:1) and injected (100 ug CCK) into laying hens. A second injection of the CCK-8 conjugate in Freund's incomplete adjuvant was injected 7 days after primary injection. A second group of control hens did not receive the CCK vaccination. Approximately 2,880 eggs were collected 5 months after the initial injection and the whole eggs were separated into egg yolk and egg white. The egg yolk was spray dried in 8 lots and the antibody titers of the blended spray dried yolk powder were measured.

Results

ELISA determinations of the CCK antibody in spray dried egg yolk showed higher end point titers when compared with negative control egg yolk (TABLE 1). Yolks from hens vaccinated with CCK-8 peptide showed an average of 1064 ug/gram in contrast to the negative control egg yolk which contained 3.4 ug/gram specific antibody against CCK-8 peptide.

TABLE 1

Analysis of Specific Anti-CCK-8 Antibody

| Sample | Average anti-CCK-8 Antibody (ug/gram yolk) | Average End Point Titer |
|---|---|---|
| Yolk from Hens Vaccinated with CCK-8 Peptide Conjugate | 1064 | 394240 |
| Negative Control Yolk | 3.4 | 3379 |

Example 2

Increased Muscle Protein by Feeding Egg Yolks Containing Anti-CCK-8 Antibody

Methods

Spray dried egg yolk containing anti-CCK-8 antibody with high titers of CCK antibody was blended onto poultry feed and fed to chickens to determine yield efficiency as a result of administering CCK antibodies. The objective of this trial was to determine both individual parts yield and total carcass yield before and after chilling. A field trial was run on 592 *Gallus domesticus* Broiler type Chickens (Ross× Hubbard; Peterson×Arbor Acre; Avian×Avian). The chickens were of mixed sex, and were started on the feed formulations at the age of one day old hatchlings. A single batch of basal ration for each formulated diet (starter, grower, and finisher) was uniformly mixed. The experimental treatments were mixed as follows:

A. Control—no CCK-8 egg yolk
B. 35.25 grams of CCK-8 egg yolk per ton of feed
C. 70.5 grams of CCK-8 egg yolk per ton of feed
D. 105.75 grams of CCK-8 egg yolk per ton of feed The CCK-8 spray dried egg yolk powder was blended in soy oil and was sprayed onto the feed pellets. Water was provided ad libitum.

A total of 160 birds were randomly selected from each treatment and each strain of bird represented in the trial. This selection contained an equal number of males (80) and females (80). All birds were selected on an average body weight for the treatment +/−100 grams.

After 47 days of feeding, the birds were humanely sacrificed by groups of pen number and sex. Each group went through processing at the same time. Bleed time was approximately 5 minutes. All birds were weighed and identified by number. The birds were then scalded at 280° F. and picked for a pre-determined time of 9 minutes. The neck and feet were cut and weighed. The following procedures were used to collect the remaining data points:

1. Weighed individual birds live;
2. Processed carcass without giblets (WOG) weight pre-chilled after removing the intestine, neck and anus (pre-chilled weight);
3. Liver, neck and gizzard were weighed;
4. Birds were then chilled as a group for 30 minutes and then weighed again (post-chilled weight);
5. The abdominal fat pad was then removed from around the gizzard and abdominal area; and
6. Each bird was individually cut up by parts: total breast; breast (breast removed from the rib cage); drum; thigh; total leg; wings; and back. All parts are calculated on the basis of pre and post-chilled.

Results

The results showed that birds who were fed daily 70 grams/ton and 105 grams/ton of CCK antibody-containing egg or fraction thereof daily for the length of their life-time showed both an increase in muscle protein yield as well as a reduction in fat production. In particular, the pre-chilled carcasses were shown to have an average increase in muscle protein yield of approximately 2% and an average fat reduction content of approximately 0.3%, both significant under industry standards.

We claim:

1. A method for increasing muscle protein in an animal, the method comprising administering to the animal an effective amount of a composition comprising a gastrointestinal neuro-modulator antibody.

2. The method of claim 1 wherein the gastrointestinal neuro-modulator antibody is selected from the group consisting of antibodies to bombesin, cholecystokinin, gastrin, somatostatin, and neuropeptide Y.

3. The method of claim 1 wherein the gastrointestinal neuro-modulator antibody is cholecystokinin antibody.

4. The method of claim 1 wherein the composition is obtained from an egg-producing animal or a milk-producing animal.

5. The method of claim 4 wherein the egg-producing animal or milk-producing animal is hyperimmunized with an antigenic or genetic vaccine.

6. The method of claim 5 wherein the antigenic vaccine comprises at least one gastrointestinal neuro-modulator.

7. The method of claim 6 wherein the gastrointestinal neuro-modulator is selected from the group consisting of bombesin, cholecystokinin, gastrin, somatostatin, and neuropeptide Y.

8. The method of claim 4 wherein the composition comprises an egg or a fraction thereof obtained from the egg-producing animal.

9. The method of claim 8 wherein the effective amount of the composition comprises approximately 0.1 to 3 eggs per day.

10. The method of claim 4 wherein the composition comprises milk colustrum or a fraction thereof.

11. The method of claim 3 wherein the effective amount of the cholecystokinin antibody ranges from 1 $\mu$g to 50 mg per animal.

12. The method of claim 1 wherein the antibody is administered parenterally, subcutaneously, intravenously, intramuscularly, intraperitoneally, intranasally or orally.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

Asp Tyr Met Gly Trp Met Asp Phe
1              5